US012051486B2

(12) United States Patent
Binhaji et al.

(10) Patent No.: US 12,051,486 B2
(45) Date of Patent: Jul. 30, 2024

(54) UTILIZING HYDRAULIC SIMULATION TO EVALUATE QUALITY OF WATER IN SALT WATER DISPOSAL SYSTEMS

(71) Applicant: Saudi Arabian Oil Company, Dhahran (SA)

(72) Inventors: Zaid A. Binhaji, Dammam (SA); Mohammed A. Alhuraifi, Al-Qatif (SA)

(73) Assignee: Saudi Arabian Oil Company, Dhahran (SA)

( * ) Notice: Subject to any disclaimer, the term of this patent is extended or adjusted under 35 U.S.C. 154(b) by 775 days.

(21) Appl. No.: 17/173,685

(22) Filed: Feb. 11, 2021

(65) Prior Publication Data
US 2022/0254455 A1    Aug. 11, 2022

(51) Int. Cl.
*G06F 30/28* (2020.01)
*C10G 33/08* (2006.01)
*G16C 20/70* (2019.01)

(52) U.S. Cl.
CPC .............. *G16C 20/70* (2019.02); *C10G 33/08* (2013.01); *G06F 30/28* (2020.01)

(58) Field of Classification Search
CPC ..... G16C 20/70; G06F 30/28; G06F 2111/10; G06F 2113/08; C10G 33/08
(Continued)

(56) References Cited

U.S. PATENT DOCUMENTS

2001/0049902 A1* 12/2001 Varadaraj ................. C09K 8/36
44/370

2012/0292025 A1* 11/2012 Stoll ....................... E21B 43/16
166/269
(Continued)

FOREIGN PATENT DOCUMENTS

| CA | 1295279 | 2/1992 |
| WO | WO 2010131113 | 11/2010 |
| WO | WO 2016033259 | 3/2016 |

OTHER PUBLICATIONS

Al-Hajri, Nasser M. et al. "Forecasting the Reliability of a Wastewater Disposal System and Predicting Future Corrective Actions using Hydraulic Simulation", 2015, Society of Petroleum Engineers, SPE-177488-MS, pp. 1-11 (Year: 2015).*

(Continued)

*Primary Examiner* — Juan C Ochoa
(74) *Attorney, Agent, or Firm* — Fish & Richardson P.C.

(57) ABSTRACT

Systems and methods include a method for oil-in-water content. A water injection hydraulic simulation model is calibrated using water disposal pressures and rates of a water disposal system of a gas oil separation plant, including generating baseline disposal pressures and disposal rates. The model is updated based on lab results estimating emulsion viscosity at different oil-in-water content levels. A sensitivity analysis is performed to evaluate changes in disposal pressures relative to the baseline in response to changes in water quality based on an oil-in-water emulsion content. Curves of disposal pressures versus disposal rates at different oil-in-water concentrations are generated using the changes in the disposal pressures. Changes in disposal pressures and disposal rates of the water disposal system are recorded, and the changes are compared against the generated curves. An oil-in-water content corresponding to a change in the disposal pressure is determined using the water injection hydraulic simulation model.

18 Claims, 4 Drawing Sheets

(58) Field of Classification Search
USPC .......................................................... 703/9, 2
See application file for complete search history.

(56) References Cited

U.S. PATENT DOCUMENTS

| 2013/0166264 A1* | 6/2013 | Usadi .................... G06F 30/20 |
| | | 703/2 |
| 2014/0244552 A1 | 8/2014 | Liu et al. |
| 2017/0152728 A1* | 6/2017 | Abou-Sayed ........... E21B 41/00 |
| 2018/0066194 A1* | 3/2018 | Soliman ................. C10G 31/06 |

OTHER PUBLICATIONS

SAIP Examination report in Saudi Arabian Appln. No. 122430650, dated Sep. 26, 2023, 13 pages (with English Translation).

* cited by examiner

UTILIZING HYDRAULIC SIMULATION TO EVALUATE QUALITY OF WATER IN SALT WATER DISPOSAL SYSTEMS

BACKGROUND

Technical Field

The present disclosure applies to evaluating the quality of disposal water from a gas-oil plant.

Background

Disposal water quality is a key element that significantly impacts the line disposal pressure. Excessive increases in produced water disposal pressure can affect oil processing capability at a Gas Oil Separation Plant (GOSP).

SUMMARY

The present disclosure describes techniques that can be used for evaluating the quality of disposal water from a gas-oil plant. In some implementations, a computer-implemented method includes the following. A water injection hydraulic simulation model is calibrated using water disposal pressures and rates of a water disposal system of a gas oil separation plant (GOSP), including generating a baseline of disposal pressures and disposal rates of the GOSP. The water injection hydraulic simulation model is updated based on lab results estimating emulsion viscosity at different oil-in-water content levels. A sensitivity analysis is performed to evaluate changes in disposal pressures at the GOSP relative to the baseline in response to changes in water quality based on an oil-in-water emulsion content. Curves of disposal pressures versus disposal rates at different oil-in-water concentrations for the GOSP are generated using the changes in the disposal pressures at the GOSP. Changes in disposal pressures and disposal rates of the water disposal system are recorded, and the changes are compared against the generated curves. An oil-in-water content corresponding to a change in the disposal pressure is determined based on the comparing and using the water injection hydraulic simulation model.

The previously described implementation is implementable using a computer-implemented method; a non-transitory, computer-readable medium storing computer-readable instructions to perform the computer-implemented method; and a computer-implemented system including a computer memory interoperably coupled with a hardware processor configured to perform the computer-implemented method, the instructions stored on the non-transitory, computer-readable medium.

The subject matter described in this specification can be implemented in particular implementations, so as to realize one or more of the following advantages. Hydraulic simulation can be used to estimate the quality of disposal water. This can be done through simulating disposal pressures at different injection rates and different emulsion stability levels. For example, an increase in disposal pressure at the same injection rate can be attributed to the presence and the stability (or tightness) of an oil-in-water emulsion. This can provide petroleum engineers with a tool to assess the presence and tightness of oil-in-water emulsions in disposal water. Such tools can be used to promptly identify deficiencies in oil-water separation at Gas Oil Separation Plants (GOSPs). Continuous improvement of oil-water separation will eliminate the increase of disposal pressure associated with oil-water emulsions in disposal water.

The details of one or more implementations of the subject matter of this specification are set forth in the Detailed Description, the accompanying drawings, and the claims. Other features, aspects, and advantages of the subject matter will become apparent from the Detailed Description, the claims, and the accompanying drawings.

DESCRIPTION OF DRAWINGS

Like reference numbers and designations in the various drawings indicate like elements.

DETAILED DESCRIPTION

The following detailed description describes techniques for using a calibrated water injection hydraulic simulation model and continuous disposal pressure and rate data from a Gas Oil Separation Plant (GOSP) to evaluate quality of disposal water by estimating oil-in-water content. Various modifications, alterations, and permutations of the disclosed implementations can be made and will be readily apparent to those of ordinary skill in the art, and the general principles defined may be applied to other implementations and applications, without departing from scope of the disclosure. In some instances, details unnecessary to obtain an understanding of the described subject matter may be omitted so as to not obscure one or more described implementations with unnecessary detail and inasmuch as such details are within the skill of one of ordinary skill in the art. The present disclosure is not intended to be limited to the described or illustrated implementations, but to be accorded the widest scope consistent with the described principles and features.

Hydraulic simulation principles can be used to qualitatively evaluate produced water quality. The techniques can focus on virtually perceiving and signifying the disposal water quality in relation to the changes in water disposal pressure. This can be done by capitalizing on a calibrated water injection hydraulic simulation model and continuously recording disposal pressure and water disposal rate data to differentiate and comprehend the reasoning behind a remarkable or significant rise in disposal pressure.

Techniques include originating and developing a structured and calibrated water injection hydraulic simulation model using steady-state multiphase flow simulation software. The techniques can include recording a baseline disposal pressure at the disposal system. Various parameters that are measured and analyzed in the lab, such as oil content in disposal water, oil-in-water emulsion viscosity, and stability index, can be incorporated in the hydraulic simulation model. Sensitivity analysis can be run to assess the disposal pressure at a particular disposal rate with respect to the water quality. A number of curves or tables can be generated that include relationships between disposal pressure versus rate at different oil-in-water concentrations. Changes in water disposal pressures and rates can be continuously and consistently monitored and logged and compared to initial generated curves to determine the oil-in-water emulsion conforming to the change in disposal pressure.

Figure 1:
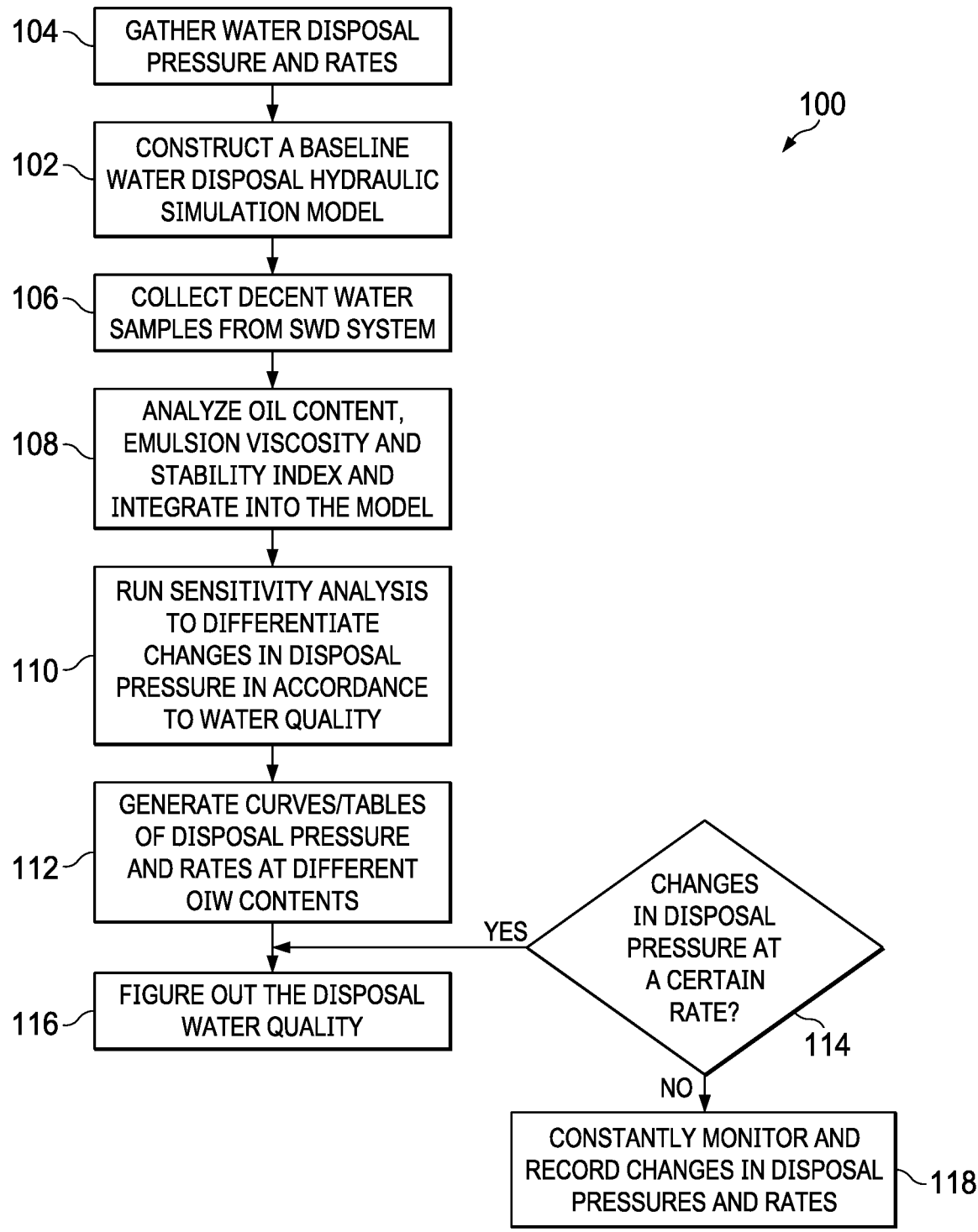
FIG. 1 is flow diagram of a workflow for qualitatively evaluating the quality of salt water, according to some implementations of the present disclosure.

FIG. 1 is flow diagram of a workflow 100 for qualitatively evaluating the quality of salt water, according to some implementations of the present disclosure. For example, the salt water can be pumped into disposal wells after being separated from crude oil in a GOSP. In some implementations, steps of the process can include the following.

At 102, a calibrated water injection hydraulic simulation model is developed using a steady-state multiphase flow simulation software. This is used to record a baseline disposal pressure at the disposal system. Constructing the baseline water disposal hydraulic simulation model can use gathered water disposal pressures and rates 104. At 106, several representative oil-in-water emulsion samples are collected. At 108, oil content, emulsion viscosity, and an emulsion stability index (ESI) are analyzed. The collection of samples can be obtained from a salt water disposal (SWD) system. The lab results are incorporated into the hydraulic simulation model. At 110, sensitivity analysis is run to evaluate and discern the change in disposal pressure at the plant in response to water quality (different concentrations of oil-in-water emulsions). At 112, various curves or tables for (disposal pressure vs. rate) are generated at different oil-in-water (OIW) contents. Changes in disposal pressure and rate are recorded continuously and compared against the generated curves. At 114, if there are changes in disposal pressure at a certain rate (or above a certain predetermined threshold pressure or a percentage change in pressure), then at 116, the oil-in-water content corresponding to the changed disposal pressure is determined. During the process, changes in disposal pressures and rates are constantly monitored and recorded at 118.

Figure 2:
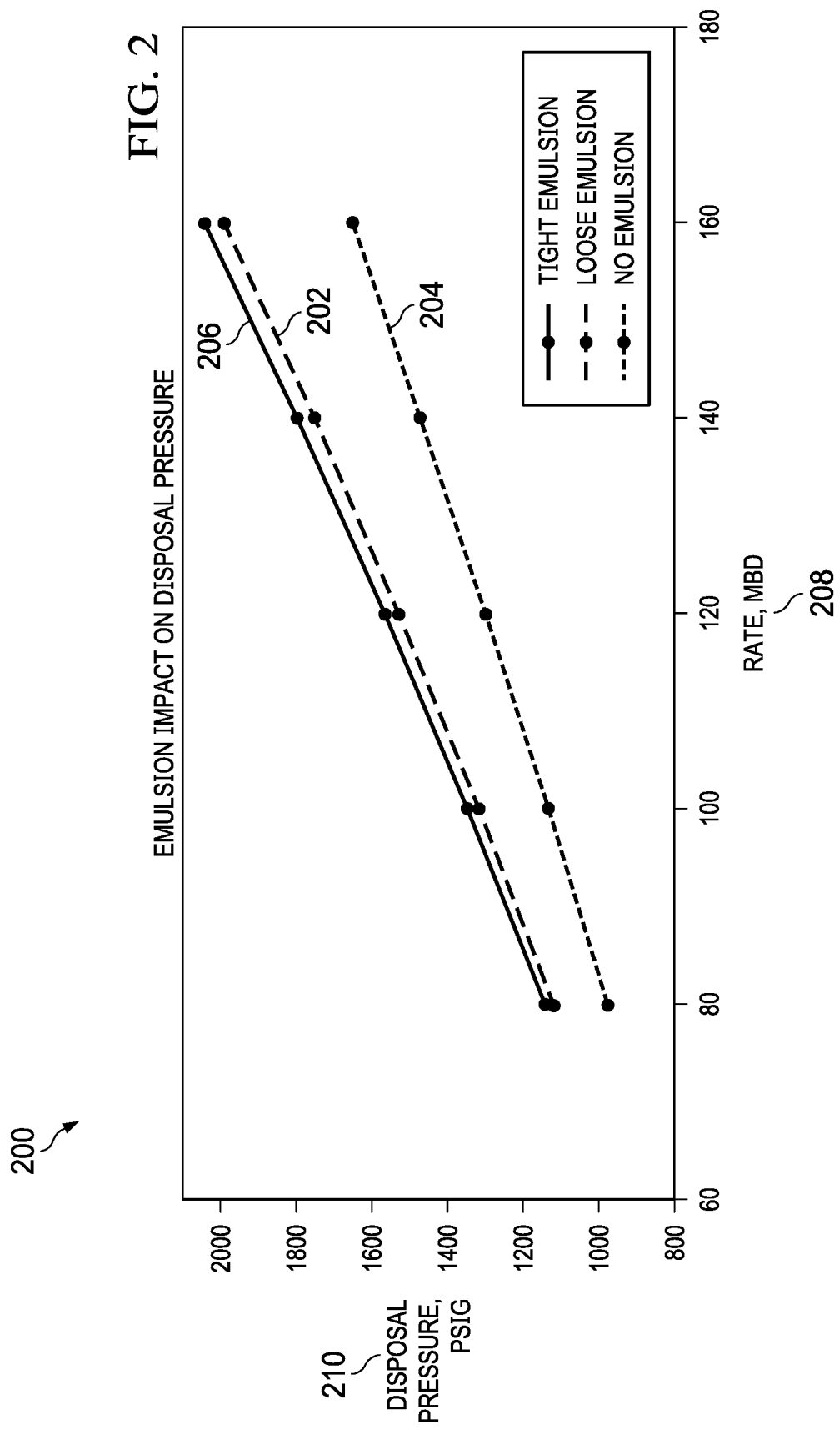
FIG. 2 is a graph showing examples of plots of emulsion impacts on disposal pressures, according to some implementations of the present disclosure.

Intermittently, disposal water that is injected into the disposal line is accompanied with oil-in-water emulsion. A resulting emulsion stability plays a vital role when it comes to disposal line pressure. For instance, stable (tight) emulsions pose higher pressure drops across the disposal lines due to a higher viscosity in comparison to the unstable (loose) emulsion (where the disposal line pressure is relatively lower). Preferably, adequate oil-water separation is desirable in which an associated oil-in-water emulsion being disposed along with the disposal water is very slim. FIG. 2 illustrates the impact of water quality on the disposal pressure and the implications of the aforementioned states and scenarios. Once the curves are generated using the simulation software, the disposal pressure level can be correlated to the viscosity of the liquid, which in turn can be used to evaluate the presence of emulsion and its stability.

FIG. 2 is a graph 200 showing examples of plots of emulsion impacts on disposal pressures, according to some implementations of the present disclosure. The graph 200 includes a loose emulsion plot 202, a no emulsion plot 204, and a tight emulsion plot 206. The plots 202, 204, and 206 are plotted relative to a disposal rate 208 (for example, in thousands of barrels per day (MBD)) and a disposal pressure 210 (for example, in pounds per square inch, gauge (PSIG)).

Figure 3:
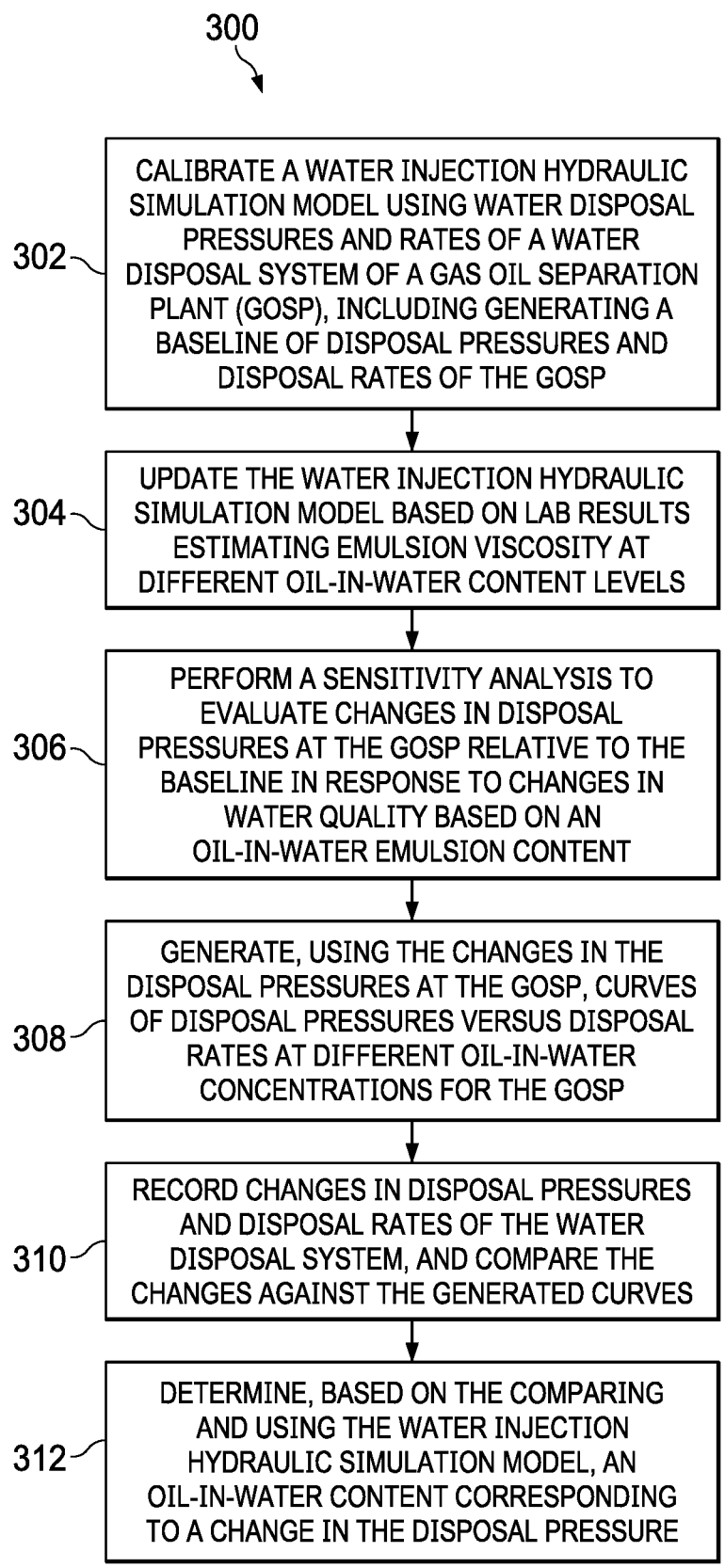
FIG. 3 is a flowchart of an example of a method for determining an oil-in-water content corresponding to a change in the disposal pressure at a water disposal system, according to some implementations of the present disclosure.

FIG. 3 is a flowchart of an example of a method 300 for determining an oil-in-water content corresponding to a change in the disposal pressure at a water disposal system, according to some implementations of the present disclosure. For clarity of presentation, the description that follows generally describes method 300 in the context of the other figures in this description. However, it will be understood that method 300 can be performed, for example, by any suitable system, environment, software, and hardware, or a combination of systems, environments, software, and hardware, as appropriate. In some implementations, various steps of method 300 can be run in parallel, in combination, in loops, or in any order.

At 302, a water injection hydraulic simulation model is calibrated using water disposal pressures and rates of a water disposal system of a GOSP, including generating a baseline of disposal pressures and disposal rates of the GOSP. As an example, the water injection hydraulic simulation model can be calibrated using steady-state multiphase flow simulation software. From 302, method 300 proceeds to 304.

At 304, the water injection hydraulic simulation model is updated based on lab results estimating emulsion viscosity at different oil-in-water content levels. The lab results can be generated, for example, by analyzing oil content, emulsion viscosity, and an ESI from representative oil-in-water emulsion samples of the GOSP. The samples can be collected from a SWD system, for example. From 304, method 300 proceeds to 306.

At 306, a sensitivity analysis is performed using the calibrated hydraulic simulation model from 302 to evaluate changes in disposal pressures at the GOSP relative to the baseline in response to changes in water quality based on an oil-in-water emulsion content. From 306, method 300 proceeds to 308.

At 308, curves of disposal pressures versus disposal rates at different oil-in-water concentrations for the GOSP are generated using the changes in the disposal pressures at the GOSP. For example, the curves shown in FIG. 2 can be generated. From 308, method 300 proceeds to 310.

At 310, changes in disposal pressures and disposal rates of the water disposal system are recorded, and the changes are compared against the generated curves. For example, the changes in disposal pressures and disposal rates of the water disposal system are recorded as described with reference to FIG. 1. From 310, method 300 proceeds to 312.

At 312, an oil-in-water content corresponding to a change in the disposal pressure is determined based on the comparing and using the water injection hydraulic simulation model. For example, the oil-in-water content can be determined as described with reference to FIG. 1. After 312, method 300 can stop.

In some implementations, method 300 further includes generating a graph plotting emulsion impacts on disposal pressures, for example, as described with reference to FIG. 2. The graph can include a loose emulsion plot, a no emulsion plot, and a tight emulsion plot, and wherein plots in the graph are plotted relative to a disposal rate and a disposal pressure. In some implementations, method 300 further includes pumping salt water into disposal wells after being separated from the crude oil in the GOSP.

Figure 4:
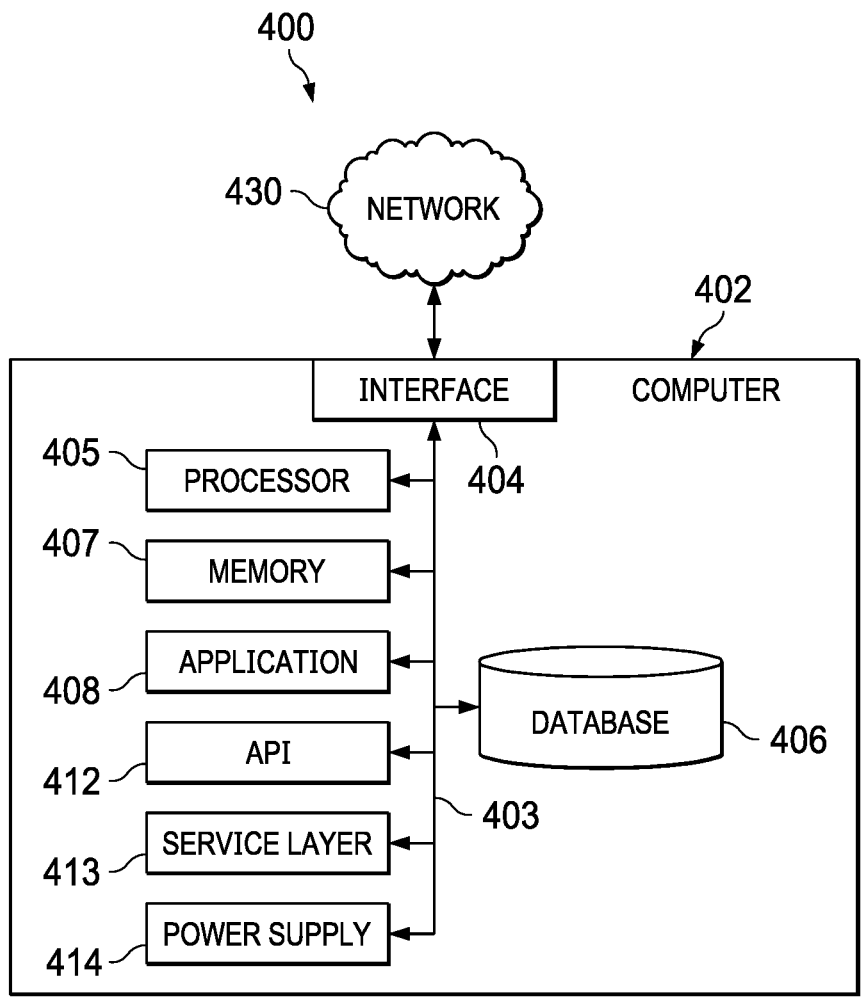
FIG. 4 is a block diagram illustrating an example computer system used to provide computational functionalities associated with described algorithms, methods, functions, processes, flows, and procedures as described in the present disclosure, according to some implementations of the present disclosure.

FIG. 4 is a block diagram of an example computer system 400 used to provide computational functionalities associated with described algorithms, methods, functions, processes, flows, and procedures described in the present disclosure, according to some implementations of the present disclosure. The illustrated computer 402 is intended to encompass any computing device such as a server, a desktop computer, a laptop/notebook computer, a wireless data port, a smart phone, a personal data assistant (PDA), a tablet computing device, or one or more processors within these devices, including physical instances, virtual instances, or both. The computer 402 can include input devices such as keypads, keyboards, and touch screens that can accept user information. Also, the computer 402 can include output devices that can convey information associated with the operation of the computer 402. The information can include digital data, visual data, audio information, or a combination of information. The information can be presented in a graphical user interface (UI) (or GUI).

The computer 402 can serve in a role as a client, a network component, a server, a database, a persistency, or components of a computer system for performing the subject matter described in the present disclosure. The illustrated computer 402 is communicably coupled with a network 430. In some implementations, one or more components of the computer 402 can be configured to operate within different environments, including cloud-computing-based environments, local environments, global environments, and combinations of environments.

At a top level, the computer 402 is an electronic computing device operable to receive, transmit, process, store, and manage data and information associated with the described subject matter. According to some implementations, the computer 402 can also include, or be communicably coupled with, an application server, an email server, a web server, a caching server, a streaming data server, or a combination of servers.

The computer 402 can receive requests over network 430 from a client application (for example, executing on another computer 402). The computer 402 can respond to the received requests by processing the received requests using software applications. Requests can also be sent to the computer 402 from internal users (for example, from a command console), external (or third) parties, automated applications, entities, individuals, systems, and computers.

Each of the components of the computer 402 can communicate using a system bus 403. In some implementations, any or all of the components of the computer 402, including hardware or software components, can interface with each other or the interface 404 (or a combination of both) over the system bus 403. Interfaces can use an application programming interface (API) 412, a service layer 413, or a combination of the API 412 and service layer 413. The API 412 can include specifications for routines, data structures, and object classes. The API 412 can be either computer-language independent or dependent. The API 412 can refer to a complete interface, a single function, or a set of APIs.

The service layer 413 can provide software services to the computer 402 and other components (whether illustrated or not) that are communicably coupled to the computer 402. The functionality of the computer 402 can be accessible for all service consumers using this service layer. Software services, such as those provided by the service layer 413, can provide reusable, defined functionalities through a defined interface. For example, the interface can be software written in JAVA, C++, or a language providing data in extensible markup language (XML) format. While illustrated as an integrated component of the computer 402, in alternative implementations, the API 412 or the service layer 413 can be stand-alone components in relation to other components of the computer 402 and other components communicably coupled to the computer 402. Moreover, any or all parts of the API 412 or the service layer 413 can be implemented as child or sub-modules of another software module, enterprise application, or hardware module without departing from the scope of the present disclosure.

The computer 402 includes an interface 404. Although illustrated as a single interface 404 in FIG. 4, two or more interfaces 404 can be used according to particular needs, desires, or particular implementations of the computer 402 and the described functionality. The interface 404 can be used by the computer 402 for communicating with other systems that are connected to the network 430 (whether illustrated or not) in a distributed environment. Generally, the interface 404 can include, or be implemented using, logic encoded in software or hardware (or a combination of software and hardware) operable to communicate with the network 430. More specifically, the interface 404 can include software supporting one or more communication protocols associated with communications. As such, the network 430 or the interface's hardware can be operable to communicate physical signals within and outside of the illustrated computer 402.

The computer 402 includes a processor 405. Although illustrated as a single processor 405 in FIG. 4, two or more processors 405 can be used according to particular needs, desires, or particular implementations of the computer 402 and the described functionality. Generally, the processor 405 can execute instructions and can manipulate data to perform the operations of the computer 402, including operations using algorithms, methods, functions, processes, flows, and procedures as described in the present disclosure.

The computer 402 also includes a database 406 that can hold data for the computer 402 and other components connected to the network 430 (whether illustrated or not). For example, database 406 can be an in-memory, conventional, or a database storing data consistent with the present disclosure. In some implementations, database 406 can be a combination of two or more different database types (for example, hybrid in-memory and conventional databases) according to particular needs, desires, or particular implementations of the computer 402 and the described functionality. Although illustrated as a single database 406 in FIG. 4, two or more databases (of the same, different, or combination of types) can be used according to particular needs, desires, or particular implementations of the computer 402 and the described functionality. While database 406 is illustrated as an internal component of the computer 402, in alternative implementations, database 406 can be external to the computer 402.

The computer 402 also includes a memory 407 that can hold data for the computer 402 or a combination of components connected to the network 430 (whether illustrated or not). Memory 407 can store any data consistent with the present disclosure. In some implementations, memory 407 can be a combination of two or more different types of memory (for example, a combination of semiconductor and magnetic storage) according to particular needs, desires, or particular implementations of the computer 402 and the described functionality. Although illustrated as a single memory 407 in FIG. 4, two or more memories 407 (of the same, different, or combination of types) can be used according to particular needs, desires, or particular implementations of the computer 402 and the described functionality. While memory 407 is illustrated as an internal component of the computer 402, in alternative implementations, memory 407 can be external to the computer 402.

The application 408 can be an algorithmic software engine providing functionality according to particular needs, desires, or particular implementations of the computer 402 and the described functionality. For example, application 408 can serve as one or more components, modules, or applications. Further, although illustrated as a single application 408, the application 408 can be implemented as multiple applications 408 on the computer 402. In addition, although illustrated as internal to the computer 402, in alternative implementations, the application 408 can be external to the computer 402.

The computer 402 can also include a power supply 414. The power supply 414 can include a rechargeable or non-rechargeable battery that can be configured to be either user- or non-user-replaceable. In some implementations, the power supply 414 can include power-conversion and management circuits, including recharging, standby, and power management functionalities. In some implementations, the power-supply 414 can include a power plug to allow the computer 402 to be plugged into a wall socket or a power source to, for example, power the computer 402 or recharge a rechargeable battery.

There can be any number of computers 402 associated with, or external to, a computer system containing computer 402, with each computer 402 communicating over network 430. Further, the terms "client," "user," and other appropriate terminology can be used interchangeably, as appropriate, without departing from the scope of the present disclosure. Moreover, the present disclosure contemplates that many users can use one computer 402 and one user can use multiple computers 402.

Described implementations of the subject matter can include one or more features, alone or in combination.

For example, in a first implementation, a computer-implemented method includes the following. A water injection hydraulic simulation model is calibrated using water disposal pressures and rates of a water disposal system of a gas oil separation plant (GOSP), including generating a baseline of disposal pressures and disposal rates of the GOSP. The water injection hydraulic simulation model is updated based on lab results estimating emulsion viscosity at different oil-in-water content levels. A sensitivity analysis is performed to evaluate changes in disposal pressures at the GOSP relative to the baseline in response to changes in water quality based on an oil-in-water emulsion content. Curves of disposal pressures versus disposal rates at different oil-in-water concentrations for the GOSP are generated using the changes in the disposal pressures at the GOSP. Changes in disposal pressures and disposal rates of the water disposal system are recorded, and the changes are compared against the generated curves. An oil-in-water content corresponding to a change in the disposal pressure is determined based on the comparing and using the water injection hydraulic simulation model.

The foregoing and other described implementations can each, optionally, include one or more of the following features:

A first feature, combinable with any of the following features, where calibrating the water injection hydraulic simulation model uses steady-state multiphase flow simulation software.

A second feature, combinable with any of the previous or following features, further including generating a graph plotting emulsion impacts on disposal pressures.

A third feature, combinable with any of the previous or following features, where the graph includes a loose emulsion plot, a no emulsion plot, and a tight emulsion plot, and wherein plots in the graph are plotted relative to a disposal rate and a disposal pressure.

A fourth feature, combinable with any of the previous or following features, further including generating lab results by analyzing oil content, emulsion viscosity, and an emulsion stability index (ESI) from representative oil-in-water emulsion samples of the GOSP.

A fifth feature, combinable with any of the previous or following features, further including collecting the samples from a salt water disposal (SWD) system.

A sixth feature, combinable with any of the previous or following features, further including pumping salt water into disposal wells after being separated from the crude oil in the GOSP.

In a second implementation, a non-transitory, computer-readable medium stores one or more instructions executable by a computer system to perform operations including the following. A water injection hydraulic simulation model is calibrated using water disposal pressures and rates of a water disposal system of a gas oil separation plant (GOSP), including generating a baseline of disposal pressures and disposal rates of the GOSP. The water injection hydraulic simulation model is updated based on lab results estimating emulsion viscosity at different oil-in-water content levels. A sensitivity analysis is performed to evaluate changes in disposal pressures at the GOSP relative to the baseline in response to changes in water quality based on an oil-in-water emulsion content. Curves of disposal pressures versus disposal rates at different oil-in-water concentrations for the GOSP are generated using the changes in the disposal pressures at the GOSP. Changes in disposal pressures and disposal rates of the water disposal system are recorded, and the changes are compared against the generated curves. An oil-in-water content corresponding to a change in the disposal pressure is determined based on the comparing and using the water injection hydraulic simulation model.

The foregoing and other described implementations can each, optionally, include one or more of the following features:

A first feature, combinable with any of the following features, where calibrating the water injection hydraulic simulation model uses steady-state multiphase flow simulation software.

A second feature, combinable with any of the previous or following features, the operations further including generating a graph plotting emulsion impacts on disposal pressures.

A third feature, combinable with any of the previous or following features, where the graph includes a loose emulsion plot, a no emulsion plot, and a tight emulsion plot, and wherein plots in the graph are plotted relative to a disposal rate and a disposal pressure.

A fourth feature, combinable with any of the previous or following features, the operations further including generating lab results by analyzing oil content, emulsion viscosity, and an emulsion stability index (ESI) from representative oil-in-water emulsion samples of the GOSP.

A fifth feature, combinable with any of the previous or following features, the operations further including collecting the samples from a salt water disposal (SWD) system.

A sixth feature, combinable with any of the previous or following features, the operations further including pumping salt water into disposal wells after being separated from the crude oil in the GOSP.

In a third implementation, a computer-implemented system includes one or more processors and a non-transitory computer-readable storage medium coupled to the one or more processors and storing programming instructions for execution by the one or more processors. The programming instructions instruct the one or more processors to perform operations including the following. A water injection hydraulic simulation model is calibrated using water disposal pressures and rates of a water disposal system of a gas oil separation plant (GOSP), including generating a baseline of disposal pressures and disposal rates of the GOSP. The water injection hydraulic simulation model is updated based on lab results estimating emulsion viscosity at different oil-in-water content levels. A sensitivity analysis is performed to evaluate changes in disposal pressures at the GOSP relative to the baseline in response to changes in water quality based on an oil-in-water emulsion content. Curves of disposal pressures versus disposal rates at different oil-in-water concentrations for the GOSP are generated using the changes in the disposal pressures at the GOSP. Changes in disposal pressures and disposal rates of the water disposal system are recorded, and the changes are compared against the generated curves. An oil-in-water content corresponding to a change in the disposal pressure is determined based on the comparing and using the water injection hydraulic simulation model.

The foregoing and other described implementations can each, optionally, include one or more of the following features:

A first feature, combinable with any of the following features, where calibrating the water injection hydraulic simulation model uses steady-state multiphase flow simulation software.

A second feature, combinable with any of the previous or following features, the operations further including generating a graph plotting emulsion impacts on disposal pressures.

A third feature, combinable with any of the previous or following features, where the graph includes a loose emulsion plot, a no emulsion plot, and a tight emulsion plot, and wherein plots in the graph are plotted relative to a disposal rate and a disposal pressure.

A fourth feature, combinable with any of the previous or following features, the operations further including generating lab results by analyzing oil content, emulsion viscosity, and an emulsion stability index (ESI) from representative oil-in-water emulsion samples of the GOSP.

A fifth feature, combinable with any of the previous or following features, the operations further including collecting the samples from a salt water disposal (SWD) system.

Implementations of the subject matter and the functional operations described in this specification can be implemented in digital electronic circuitry, in tangibly embodied computer software or firmware, in computer hardware, including the structures disclosed in this specification and their structural equivalents, or in combinations of one or more of them. Software implementations of the described subject matter can be implemented as one or more computer programs. Each computer program can include one or more modules of computer program instructions encoded on a tangible, non-transitory, computer-readable computer-storage medium for execution by, or to control the operation of, data processing apparatus. Alternatively, or additionally, the program instructions can be encoded in/on an artificially generated propagated signal. For example, the signal can be a machine-generated electrical, optical, or electromagnetic signal that is generated to encode information for transmission to a suitable receiver apparatus for execution by a data processing apparatus. The computer-storage medium can be a machine-readable storage device, a machine-readable storage substrate, a random or serial access memory device, or a combination of computer-storage mediums.

The terms "data processing apparatus," "computer," and "electronic computer device" (or equivalent as understood by one of ordinary skill in the art) refer to data processing hardware. For example, a data processing apparatus can encompass all kinds of apparatuses, devices, and machines for processing data, including by way of example, a programmable processor, a computer, or multiple processors or computers. The apparatus can also include special purpose logic circuitry including, for example, a central processing unit (CPU), a field-programmable gate array (FPGA), or an application-specific integrated circuit (ASIC). In some implementations, the data processing apparatus or special purpose logic circuitry (or a combination of the data processing apparatus or special purpose logic circuitry) can be hardware- or software-based (or a combination of both hardware- and software-based). The apparatus can optionally include code that creates an execution environment for computer programs, for example, code that constitutes processor firmware, a protocol stack, a database management system, an operating system, or a combination of execution environments. The present disclosure contemplates the use of data processing apparatuses with or without conventional operating systems, such as LINUX, UNIX, WINDOWS, MAC OS, ANDROID, or IOS.

A computer program, which can also be referred to or described as a program, software, a software application, a module, a software module, a script, or code, can be written in any form of programming language. Programming languages can include, for example, compiled languages, interpreted languages, declarative languages, or procedural languages. Programs can be deployed in any form, including as stand-alone programs, modules, components, subroutines, or units for use in a computing environment. A computer program can, but need not, correspond to a file in a file system. A program can be stored in a portion of a file that holds other programs or data, for example, one or more scripts stored in a markup language document, in a single file dedicated to the program in question, or in multiple coordinated files storing one or more modules, sub-programs, or portions of code. A computer program can be deployed for execution on one computer or on multiple computers that are located, for example, at one site or distributed across multiple sites that are interconnected by a communication network. While portions of the programs illustrated in the various figures may be shown as individual modules that implement the various features and functionality through various objects, methods, or processes, the programs can instead include a number of sub-modules, third-party services, components, and libraries. Conversely, the features and functionality of various components can be combined into single components as appropriate. Thresholds used to make computational determinations can be statically, dynamically, or both statically and dynamically determined.

The methods, processes, or logic flows described in this specification can be performed by one or more programmable computers executing one or more computer programs to perform functions by operating on input data and generating output. The methods, processes, or logic flows can also be performed by, and apparatus can also be implemented as, special purpose logic circuitry, for example, a CPU, an FPGA, or an ASIC.

Computers suitable for the execution of a computer program can be based on one or more of general and special purpose microprocessors and other kinds of CPUs. The elements of a computer are a CPU for performing or executing instructions and one or more memory devices for storing instructions and data. Generally, a CPU can receive instructions and data from (and write data to) a memory.

Graphics processing units (GPUs) can also be used in combination with CPUs. The GPUs can provide specialized processing that occurs in parallel to processing performed by CPUs. The specialized processing can include artificial intelligence (AI) applications and processing, for example. GPUs can be used in GPU clusters or in multi-GPU computing.

A computer can include, or be operatively coupled to, one or more mass storage devices for storing data. In some implementations, a computer can receive data from, and transfer data to, the mass storage devices including, for example, magnetic, magneto-optical disks, or optical disks. Moreover, a computer can be embedded in another device, for example, a mobile telephone, a personal digital assistant (PDA), a mobile audio or video player, a game console, a global positioning system (GPS) receiver, or a portable storage device such as a universal serial bus (USB) flash drive.

Computer-readable media (transitory or non-transitory, as appropriate) suitable for storing computer program instructions and data can include all forms of permanent/non-permanent and volatile/non-volatile memory, media, and memory devices. Computer-readable media can include, for example, semiconductor memory devices such as random access memory (RAM), read-only memory (ROM), phase change memory (PRAM), static random access memory (SRAM), dynamic random access memory (DRAM), erasable programmable read-only memory (EPROM), electrically erasable programmable read-only memory (EEPROM), and flash memory devices. Computer-readable media can also include, for example, magnetic devices such as tape, cartridges, cassettes, and internal/removable disks. Computer-readable media can also include magneto-optical disks and optical memory devices and technologies including, for example, digital video disc (DVD), CD-ROM, DVD+/−R, DVD-RAM, DVD-ROM, HD-DVD, and BLU-RAY. The memory can store various objects or data, including caches, classes, frameworks, applications, modules, backup data, jobs, web pages, web page templates, data structures, database tables, repositories, and dynamic information. Types of objects and data stored in memory can include parameters, variables, algorithms, instructions, rules, constraints, and references. Additionally, the memory can include logs, policies, security or access data, and reporting files. The processor and the memory can be supplemented by, or incorporated into, special purpose logic circuitry.

Implementations of the subject matter described in the present disclosure can be implemented on a computer having a display device for providing interaction with a user, including displaying information to (and receiving input from) the user. Types of display devices can include, for example, a cathode ray tube (CRT), a liquid crystal display (LCD), a light-emitting diode (LED), and a plasma monitor. Display devices can include a keyboard and pointing devices including, for example, a mouse, a trackball, or a trackpad. User input can also be provided to the computer through the use of a touchscreen, such as a tablet computer surface with pressure sensitivity or a multi-touch screen using capacitive or electric sensing. Other kinds of devices can be used to provide for interaction with a user, including to receive user feedback including, for example, sensory feedback including visual feedback, auditory feedback, or tactile feedback. Input from the user can be received in the form of acoustic, speech, or tactile input. In addition, a computer can interact with a user by sending documents to, and receiving documents from, a device that the user uses. For example, the computer can send web pages to a web browser on a user's client device in response to requests received from the web browser.

The term "graphical user interface," or "GUI," can be used in the singular or the plural to describe one or more graphical user interfaces and each of the displays of a particular graphical user interface. Therefore, a GUI can represent any graphical user interface, including, but not limited to, a web browser, a touch-screen, or a command line interface (CLI) that processes information and efficiently presents the information results to the user. In general, a GUI can include a plurality of user interface (UI) elements, some or all associated with a web browser, such as interactive fields, pull-down lists, and buttons. These and other UI elements can be related to or represent the functions of the web browser.

Implementations of the subject matter described in this specification can be implemented in a computing system that includes a back-end component, for example, as a data server, or that includes a middleware component, for example, an application server. Moreover, the computing system can include a front-end component, for example, a client computer having one or both of a graphical user interface or a Web browser through which a user can interact with the computer. The components of the system can be interconnected by any form or medium of wireline or wireless digital data communication (or a combination of data communication) in a communication network. Examples of communication networks include a local area network (LAN), a radio access network (RAN), a metropolitan area network (MAN), a wide area network (WAN), Worldwide Interoperability for Microwave Access (WIMAX), a wireless local area network (WLAN) (for example, using 802.11 a/b/g/n or 802.20 or a combination of protocols), all or a portion of the Internet, or any other communication system or systems at one or more locations (or a combination of communication networks). The network can communicate with, for example, Internet Protocol (IP) packets, frame relay frames, asynchronous transfer mode (ATM) cells, voice, video, data, or a combination of communication types between network addresses.

The computing system can include clients and servers. A client and server can generally be remote from each other and can typically interact through a communication network. The relationship of client and server can arise by virtue of computer programs running on the respective computers and having a client-server relationship.

Cluster file systems can be any file system type accessible from multiple servers for read and update. Locking or consistency tracking may not be necessary since the locking of exchange file system can be done at application layer. Furthermore, Unicode data files can be different from non-Unicode data files.

While this specification contains many specific implementation details, these should not be construed as limitations on the scope of what may be claimed, but rather as descriptions of features that may be specific to particular implementations. Certain features that are described in this specification in the context of separate implementations can also be implemented, in combination, in a single implementation. Conversely, various features that are described in the context of a single implementation can also be implemented in multiple implementations, separately, or in any suitable sub-combination. Moreover, although previously described features may be described as acting in certain combinations and even initially claimed as such, one or more features from a claimed combination can, in some cases, be excised from the combination, and the claimed combination may be directed to a sub-combination or variation of a sub-combination.

Particular implementations of the subject matter have been described. Other implementations, alterations, and permutations of the described implementations are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results. In certain circumstances, multitasking or parallel processing (or a combination of multitasking and parallel processing) may be advantageous and performed as deemed appropriate.

Moreover, the separation or integration of various system modules and components in the previously described implementations should not be understood as requiring such separation or integration in all implementations. It should be understood that the described program components and systems can generally be integrated together in a single software product or packaged into multiple software products.

Accordingly, the previously described example implementations do not define or constrain the present disclosure. Other changes, substitutions, and alterations are also possible without departing from the spirit and scope of the present disclosure.

Furthermore, any claimed implementation is considered to be applicable to at least a computer-implemented method; a non-transitory, computer-readable medium storing computer-readable instructions to perform the computer-implemented method; and a computer system including a computer memory interoperably coupled with a hardware processor configured to perform the computer-implemented method or the instructions stored on the non-transitory, computer-readable medium.

What is claimed is:

1. A computer-implemented method, comprising:
    calibrating a water injection hydraulic simulation model using water disposal pressures and rates of a water disposal system of a gas oil separation plant (GOSP), to generate a baseline of disposal pressures and disposal rates of the GOSP;
    updating the water injection hydraulic simulation model based on lab results obtained from a salt water disposal system, the lab results estimating oil content, emulsion viscosity, and an emulsion stability index at different oil-in-water content levels;
    performing a sensitivity analysis to evaluate changes in disposal pressures at the GOSP relative to the baseline in response to changes in water quality based on an oil-in-water emulsion content;
    generating using the changes in the disposal pressures at the GOSP, curves of disposal pressures versus disposal rates at different oil-in-water concentrations for the GOSP;
    recording changes in disposal pressures and disposal rates of the water disposal system, and comparing the changes against the curves to generate comparison results;
    determining, based on the comparison results and using the water injection hydraulic simulation model, an oil-in-water content corresponding to a change in the disposal pressures to determine that salt water is separated from crude oil in the GOSP; and
    pumping the salt water separated from the crude oil into disposal wells.

2. The computer-implemented method of claim 1, wherein calibrating the water injection hydraulic simulation model uses steady-state multiphase flow simulation software.

3. The computer-implemented method of claim 1, further comprising generating a graph plotting emulsion impacts on disposal pressures.

4. The computer-implemented method of claim 3, wherein the graph comprises a no emulsion plot, and an emulsion plot, and wherein plots in the graph are plotted relative to a disposal rate and a disposal pressure.

5. The computer-implemented method of claim 1, wherein the changes in disposal pressures are compared to a threshold pressure or a percentage change in pressure to generate the comparison results.

6. The computer-implemented method of claim 1, further comprising collecting samples from a salt water disposal (SWD) system.

7. A non-transitory, computer-readable medium storing one or more instructions executable by a computer system to perform operations comprising:
    calibrating a water injection hydraulic simulation model using water disposal pressures and rates of a water disposal system of a gas oil separation plant (GOSP), to generate a baseline of disposal pressures and disposal rates of the GOSP;
    updating the water injection hydraulic simulation model based on lab results obtained from a salt water disposal system, the lab results estimating oil content, emulsion viscosity, and an emulsion stability index at different oil-in-water content levels;
    performing a sensitivity analysis to evaluate changes in disposal pressures at the GOSP relative to the baseline in response to changes in water quality based on an oil-in-water emulsion content;
    generating using the changes in the disposal pressures at the GOSP, curves of disposal pressures versus disposal rates at different oil-in-water concentrations for the GOSP;
    recording changes in disposal pressures and disposal rates of the water disposal system, and comparing the changes against the curves to generate comparison results;
    determining, based on the comparison results and using the water injection hydraulic simulation model, an oil-in-water content corresponding to a change in the disposal pressures to determine that salt water is separated from crude oil in the GOSP; and
    pumping the salt water separated from the crude oil into disposal wells.

8. The non-transitory, computer-readable medium of claim 7, wherein calibrating the water injection hydraulic simulation model uses steady-state multiphase flow simulation software.

9. The non-transitory, computer-readable medium of claim 7, the operations further comprising generating a graph plotting emulsion impacts on disposal pressures.

10. The non-transitory, computer-readable medium of claim 9, wherein the graph comprises a no emulsion plot, and an emulsion plot, and wherein plots in the graph are plotted relative to a disposal rate and a disposal pressure.

11. The non-transitory, computer-readable medium of claim 7, wherein the changes in disposal pressures are compared to a threshold pressure or a percentage change in pressure to generate the comparison results.

12. The non-transitory, computer-readable medium of claim 7, the operations further comprising collecting samples from a salt water disposal (SWD) system.

13. A computer-implemented system, comprising:
one or more processors; and
a non-transitory computer-readable storage medium coupled to the one or more processors and storing programming instructions for execution by the one or more processors, the programming instructions instructing the one or more processors to perform operations comprising:
calibrating a water injection hydraulic simulation model using water disposal pressures and rates of a water disposal system of a gas oil separation plant (GOSP), to generate a baseline of disposal pressures and disposal rates of the GOSP;
updating the water injection hydraulic simulation model based on lab results obtained from a salt water disposal system, the lab results estimating oil content, emulsion viscosity, and an emulsion stability index at different oil-in-water content levels;
performing a sensitivity analysis to evaluate changes in disposal pressures at the GOSP relative to the baseline in response to changes in water quality based on an oil-in-water emulsion content;
generating using the changes in the disposal pressures at the GOSP, curves of disposal pressures versus disposal rates at different oil-in-water concentrations for the GOSP;
recording changes in disposal pressures and disposal rates of the water disposal system, and comparing the changes against the curves to generate comparison results;
determining, based on the comparison results and using the water injection hydraulic simulation model, an oil-in-water content corresponding to a change in the disposal pressures to determine that salt water is separated from crude oil in the GOSP; and
pumping the salt water separated from the crude oil into disposal wells.

14. The computer-implemented system of claim 13, wherein calibrating the water injection hydraulic simulation model uses steady-state multiphase flow simulation software.

15. The computer-implemented system of claim 13, the operations further comprising generating a graph plotting emulsion impacts on disposal pressures.

16. The computer-implemented system of claim 15, wherein the graph comprises a no emulsion plot, and an emulsion plot, and wherein plots in the graph are plotted relative to a disposal rate and a disposal pressure.

17. The computer-implemented system of claim 13, wherein the changes in disposal pressures are compared to a threshold pressure or a percentage change in pressure to generate the comparison results.

18. The computer-implemented system of claim 13, the operations further comprising collecting samples from a salt water disposal (SWD) system.

* * * * *